United States Patent
Caldera et al.

(10) Patent No.: US 6,986,766 B2
(45) Date of Patent: *Jan. 17, 2006

(54) METHOD OF ENDOVENOUS LASER TREATMENT

(75) Inventors: Tiziano Caldera, Cambs (GB); Robert Min, New York, NY (US); Peter Klein, West Newbury, MA (US)

(73) Assignee: Diomed Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/172,636

(22) Filed: Jun. 14, 2002

(65) Prior Publication Data

US 2003/0078569 A1 Apr. 24, 2003

Related U.S. Application Data

(60) Provisional application No. 60/369,256, filed on Mar. 27, 2002.

(30) Foreign Application Priority Data

Jun. 15, 2001 (GB) .............................................. 0114687

(51) Int. Cl.
*A61B 18/18* (2006.01)

(52) U.S. Cl. ............................... 606/15; 606/7; 607/88; 604/21; 128/898

(58) Field of Classification Search ................. 606/3–6, 606/13–17, 78; 607/88, 89; 604/19–21; 128/898
See application file for complete search history.

(56) References Cited

U.S. PATENT DOCUMENTS

| | | | |
|---|---|---|---|
| 4,444,185 A | | 4/1984 | Shugar |
| 4,616,656 A | | 10/1986 | Nicholson et al. |
| 5,445,608 A | * | 8/1995 | Chen et al. .................. 604/20 |
| 5,454,374 A | * | 10/1995 | Omachi ...................... 600/486 |
| 5,469,524 A | * | 11/1995 | Esch et al. .................. 385/118 |
| 5,603,710 A | * | 2/1997 | Easley et al. ................. 606/15 |
| 5,688,246 A | | 11/1997 | Waitz et al. |
| 5,766,164 A | * | 6/1998 | Mueller et al. ............... 606/15 |
| 5,796,905 A | * | 8/1998 | Hoffart et al. .............. 385/128 |

(Continued)

FOREIGN PATENT DOCUMENTS

| | | |
|---|---|---|
| EP | 0266858 | 5/1988 |
| EP | 0891157 B1 | 1/1999 |
| FR | 2793565 | 11/2000 |
| WO | WO00/19919 | 4/2000 |

OTHER PUBLICATIONS

Endovenous Laser: A New Minimally Invasive Method of Treatment for Varicose Veins—Preliminary Observations Using an 810 nm Diode Laser, Navarro, MD, et al. Dermatol Surg 27:2, Feb. 2001.

(Continued)

*Primary Examiner*—A. Farah
(74) *Attorney, Agent, or Firm*—Wolf, Greenfield & Sacks, P.C.

(57) ABSTRACT

A method of endovenous laser treatment in disclosed. An introducer sheath 40 is introduced into a vein and an optical fiber 12 is introduced through the introducer sheath until a first marking 45 on the optical fiber 12 indicates that the distal end of the optical fiber 12 is substantially in alignment with the distal end of the introducer sheath 40. The introducer sheath 40 is then withdrawn relative to the optical fiber 12 until a second marking 46 on the optical fiber 12 indicates that the distal end of the optical fiber 12 extends a predetermined distance beyond the distal end of said introducer sheath 40. Laser radiation is passed down the optical fiber 12 so that laser radiation is delivered to the inner wall of the vein and the introducer sheath 40 together with the optical fiber 12 are withdrawn a certain distance along the vein.

20 Claims, 4 Drawing Sheets

U.S. PATENT DOCUMENTS

| | | | | |
|---|---|---|---|---|
| 5,855,577 | A | * | 1/1999 | Murphy-Chutorian et al. . 606/7 |
| 5,993,072 | A | * | 11/1999 | de Juan et al. ............... 385/78 |
| RE36,473 | E | * | 12/1999 | Esch et al. .................. 385/118 |
| 6,095,149 | A | | 8/2000 | Sharkey et al. ............. 128/898 |
| 6,143,019 | A | | 11/2000 | Motamedi et al. ............ 607/89 |
| 6,331,178 | B1 | * | 12/2001 | Loeb et al. ................... 606/13 |
| 6,398,777 | B1 | * | 6/2002 | Navarro et al. ................ 606/7 |
| 6,572,608 | B1 | * | 6/2003 | Lee et al. ..................... 606/15 |
| 6,802,838 | B2 | * | 10/2004 | Loeb et al. ................... 606/13 |
| 2004/0116912 | A1 | | 6/2004 | Appling |

OTHER PUBLICATIONS

This Document (Declaration of Todd R. Trumpold) Contains Confidential Information And Is Being Submitted Under Seal Pursuant To A Protective Order Entered By The Court On Jan. 26, 2005. The Parties Designating The Information As Confidential Are Diomed, Inc., Diomed Holdings Inc. And Diomed Limited.

This Document (Defendant's Local Rule 56.1 Statement) Contains Confidential Information And Is Being Submitted Under Seal Pursuant To A Protective Order Entered By The Court on Jan. 26, 2005. The Parties Designating The Information As Confidential Are Diomed, Inc., Diomed Holdings Inc. and Diomed Limited.

Defendants' Memorandum Of Law In Support Of Motion For Summary Judgment.

Declaration of Howard Root In Support of Defendants' Motion For Summary Judgment.

Declaration of Tony Jakubowski.

The Closure® Procedure Physician Self Study Course.

Min et al., "Endovenous Laser Treatment of Saphenous Vein Reflux: Long–Term Results," Aug. 2003, JVIR.

Deposition of Anthony Jakubowski, May 25, 2005.

* cited by examiner

METHOD OF ENDOVENOUS LASER TREATMENT

CROSS-REFERENCE TO RELATED APPLICATIONS

This application claims priority from U.S. Provisional Patent Application Ser. No. 60/369,256, filed Mar. 27, 2002. and from UK Patent Application Serial No. GB-0114687, filed Jun. 15, 2001, the entire contents of each application being hereby incorporated herein by reference.

BACKGROUND OF THE INVENTION

1. Field of the Invention

The present invention relates to a method of endovenous laser treatment.

2. Description of the Related Art

In certain invasive medical procedures thermal or other energy is administered to a patient with beneficial effects. For example, energy can be used to detect a tumour or a region of the body, or to destroy or denature diseased or malfunctioning body tissue. One example of this type of treatment is disclosed in U.S. Pat. No. 6,095,149 which describes the treatment of invertebral disc abnormalities with thermal energy. Other types of medical treatment utilise laser energy, for example endovenous laser treatment (EVLT), wherein laser energy is delivered to the inner wall of a vein.

Laser energy may be delivered to an area of the body by means of an optical fiber such as a bare-tipped optical fiber. However, the tips of such optical fibers could cause trauma to soft tissues. Therefore, for some invasive applications it is not desirable to insert the optical fiber directly into the body tissue. Instead, the optical fiber is typically inserted into a flexible introducer sheath which acts to guide and protect the optical fiber (and also the surrounding tissue) whilst it is being inserted into the region of the body to be treated. An introducer sheath is frequently inserted into body tissue over a guide wire and then the optical fiber can be inserted once the introducer sheath is in place in the body.

In use the introducer sheath is often positioned so that the optical fiber protrudes a few millimeters or centimeters from the end of the introducer sheath so as to deliver laser energy efficiently from the tip of the fiber to the surrounding tissue.

It is known to detect the protrusion of the optical fiber from the introducer sheath using ultrasound and/or direct visualization of a red aiming laser beam from the optical fiber through the skin. However, these methods are unsatisfactory for a number of reasons. The use of ultrasound requires additional equipment which is expensive and complicates the procedure. Visualization of the laser beam is imprecise and at best only a guide and then only in regions of the body which are sufficiently close to the surface of the skin. Therefore, conventional techniques are not suitable for use in a wide range of applications.

Furthermore, as a result of it being difficult for an operator or surgeon to determine when the distal end of the optical fiber is approaching the distal end of the introducer sheath, damage can readily occur to the soft tissues if the optical fiber is initially accidentally extended beyond the introducer sheath. As a result an operator must insert the optical fiber very slowly into the introducer sheath and must proceed cautiously at all times which makes the procedure slow.

It is therefore desired to provide an improved method of endovenous laser treatment.

SUMMARY OF THE INVENTION

According to a first aspect of the present invention, there is provided a method of endovenous laser treatment comprising the steps of:

(a) introducing an introducer sheath having a distal end and a proximal end into a vein having an inner wall;

(b) introducing an optical fiber having a distal end and a proximal end through the introducer sheath until a first marking on the optical fiber indicates that the distal end of the optical fiber is substantially in alignment with the distal end of the introducer sheath;

(c) withdrawing the introducer sheath relative to the optical fiber until a second marking on the optical fiber indicates that the distal end of the optical fiber extends a predetermined distance beyond the distal end of the introducer sheath;

(d) passing laser radiation down the optical fiber so that laser radiation is delivered to the inner wall of the vein;

(e) withdrawing the introducer sheath together with the optical fiber a certain distance along the vein; and (f) repeating steps (d) and (e) a plurality of times.

The laser radiation which is delivered to the inner wall of the vein is absorbed and thermally re-structures the vein.

The first and second markings allow an operator or surgeon to know when the distal end of the optical fiber is aligned with the end of the introducer sheath and when the distal end of the optical fiber extends beyond the introducer sheath by a predetermined amount. This enables the operator or surgeon to quickly insert the optical fiber into the introducer sheath and enables the optical fiber to be positioned in the optimum position relative to the introducer sheath without risk of damage to either the optical fiber or surrounding tissue.

The markings may comprise at least one band which extends around at least a portion of the circumference of the optical fiber.

Preferably, the two markings are separated by a distance of either about 4 cm, about 3.5 cm, about 3 cm, about 2.5 cm or about 2 cm so that in use the optical fiber will extend preferably between 2–4 cm from the end of the introducer sheath. A separation of approximately 3 cm is particularly preferred.

The minimum preferred separation (2 cm) is so as to prevent thermal damage to the introducer sheath during treatment. The maximum preferred separation (4 cm) is so as to minimize the length of the optical fiber remaining within the body once the introducer sheath has been removed from the patient's body.

The two markings or markers may differ in shape and color to aid the operator or surgeon using the device. This can make it easier to refer to the markings, for example, when teaching or explaining how to use the device to another operator or surgeon.

The markings may be engraved or embossed on the optical fiber. This enables the operator to have tactile feedback as to the position of the markings, without having to look at the optical fiber. This allows the operator to concentrate on other equipment. Furthermore, if the markings are embossed then there may be sufficient co-operation between the marking and a friction seal of the introducer sheath so as to secure them temporarily together when the introducer sheath is retracted.

The laser radiation may be delivered either in a pulsed, continuous or quasi-continuous manner.

According to one embodiment, the introducer sheath may comprise graduated markings for assisting a user to withdraw the introducer sheath at a desired rate. This rate may be defined as a distance per unit time or a distance per laser pulse. A visual and/or audible indicator may be provided to give an indication of how fast the introducer sheath should be withdrawn.

The optical fiber is preferably secured to the introducer sheath at a position wherein the first marking is substantially in alignment with the proximal end of the introducer sheath. The optical fiber and the introducer sheath may then be positioned at a desired location using ultrasound. The introducer sheath can then be released from the optical fiber and the introducer sheath withdrawn relative to the fiber optic device until the second marking in substantially in alignment with the proximal end of the introducer sheath, enabling the distal end of the optical fiber to protrude a known distance from the distal end of the introducer sheath in order to administer laser energy. The optical fiber may then be secured to the introducer sheath substantially at the position where the second marking is substantially in alignment with the proximal end of the introducer sheath, and energy from a laser energy source may then be provided to the distal end of the optical fiber. The optical fiber and the introducer sheath may be withdrawn whilst laser energy is emitted from the distal end of the optical fiber. This is an advantageous way of administering laser energy invasively.

According to a second aspect of the present invention, there is provided a method of endovenous laser treatment comprising the steps of:

(a) introducing an introducer sheath into the Greater Saphenous Vein having an inner wall;

(b) introducing an optical fiber having a distal end and a proximal end through the introducer sheath until a marking on the optical fiber indicates that the distal end of the optical fiber extends a predetermined distance beyond the introducer sheath;

(c) passing laser radiation down the optical fiber so that laser radiation is delivered to the inner wall of the Greater Saphenous Vein;

(d) withdrawing the introducer sheath and the optical fiber along the Greater Saphenous Vein a certain distance; and (a) repeating steps (c) and (d) a plurality of times.

According to a third aspect of the present invention, there is provided a method of endovenous laser treatment comprising the steps of:

(a) introducing an introducer sheath having a distal end and a proximal end into a vein having an inner wall, the introducer sheath having graduated markings;

(b) introducing an optical fiber having a distal end and a proximal end through the introducer sheath until a first marking on the optical fiber indicates that the distal end of the optical fiber is substantially in alignment with the distal end of the introducer sheath;

(c) withdrawing the introducer sheath relative to the optical fiber until a second marking on the optical fiber indicates that the distal end of the optical fiber extends a predetermined distance beyond the distal end of the introducer sheath;

(d) continuously passing laser radiation down the optical fiber so that laser radiation is delivered to the inner wall of the vein; and (e) withdrawing the introducer sheath together with the optical fiber along the vein whilst laser radiation is passing down the optical fiber.

According to a fourth aspect of the present invention, there is provided a method of endovenous laser treatment comprising the step of:

(a) introducing an introducer sheath having a distal end and a proximal end into a vein having an inner wall;

(b) introducing an optical fiber having a distal end and a proximal end through the introducer sheath until a first marking on the optical fiber indicates that the distal end of the optical fiber is substantially in alignment with the distal end of the introducer sheath;

(c) withdrawing the introducer sheath relative to the optical fiber until a second marking on the optical fiber indicates that the distal end of the optical fiber extends a predetermined distance beyond the distal end of the introducer sheath;

(d) pulsing laser radiation down the optical fiber so that laser radiation is delivered to the inner wall of the vein;

(e) withdrawing the introducer sheath together with the optical fiber along the vein;

(f) pulsing laser radiation down the optical fiber so that laser radiation is delivered to the inner wall of the vein; and (g) withdrawing the introducer sheath together with the optical fiber along the vein.

BRIEF DESCRIPTION OF THE DRAWINGS

Various embodiment of the present invention will now described, by way of example only, and with reference to the accompanying drawings in which.

DETAILED DESCRIPTION OF THE INVENTION

Figure 1:
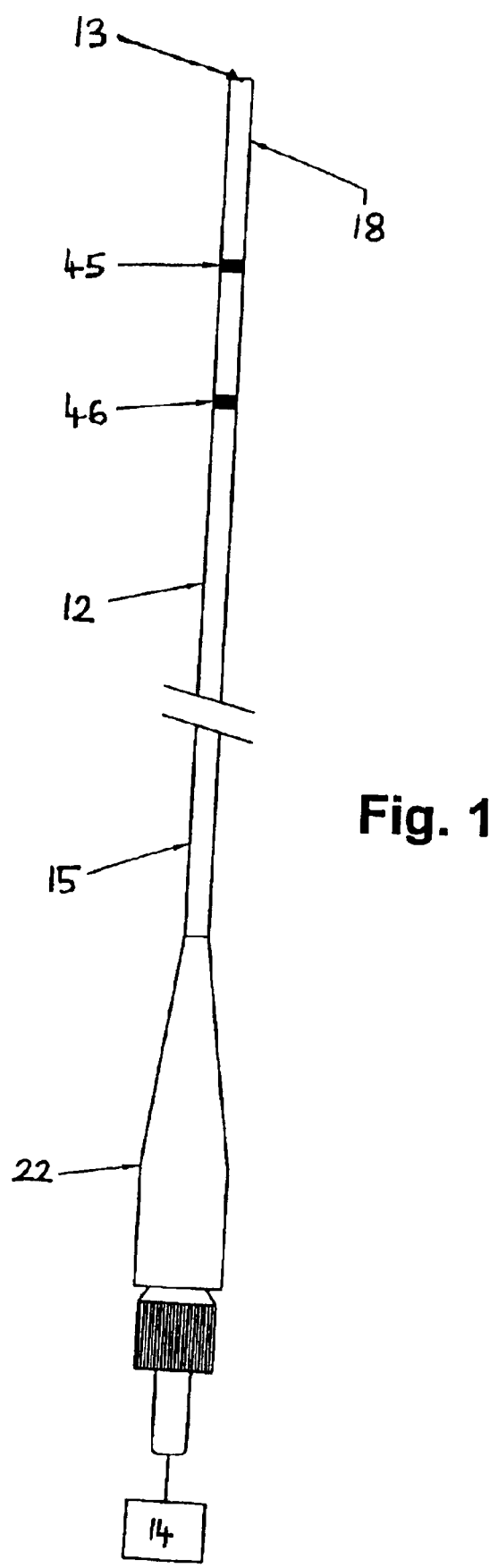
FIG. 1 shows a medical laser device.
Figure 2:
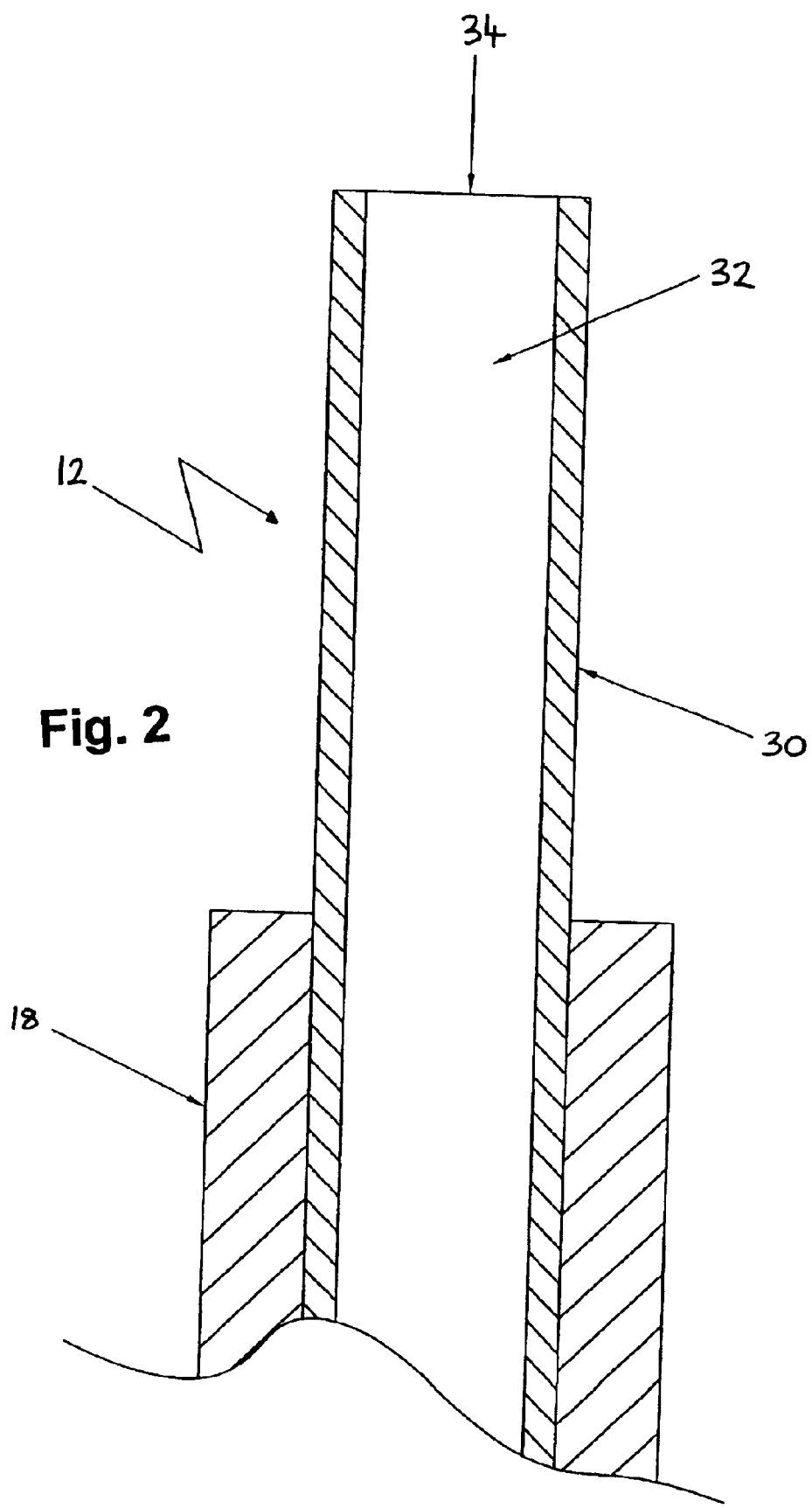
FIG. 2 shows in greater detail the distal end section of the optical fiber shown FIG. 1.

With reference to FIGS. 1 and 2, an optical fiber 12 having a distal end 13 and a proximal and 15 is shown which is coupled to a laser energy source 14 via a connector 22. According to one embodiment the optical fiber 12 has a length of 3.5 m±0.1 m and is preferably provided with a protective buffer layer 18. One or mare markings or other form of indicator 45, 46 are arranged on the optical fiber 12 at a predetermined distance from distal end 13. Preferably, the markings 45, 46 are provided around substantially the whole circumference of the protective buffer layer 18 of the optical fiber 12. According to the preferred embodiment, the laser energy source 14 is an 810 nm diode laser manufactured by DIOMED, Ltd., United Kingdom. The connector 22 may be any suitable connector/fiber terminator such as a standard sub-miniature A (SMA) connector (as shown) or other proprietary connector.

The distal end 13 of the optical fiber 12 is shown in more detail in FIG. 2. The optical fiber 12 is preferably capable of withstanding environmental temperatures of −10° C. to 120° C. and comprises a glass core 32 with a fiber tip 34, a cladding layer 30 surrounding the core 32, and an outer protective buffer layer 18. The core 32 has a higher refractive index than the cladding 30 and thus laser energy is guided along the core 32 by total internal reflection. According to the preferred embodiment the optical fiber 12 has a 600 pm diameter glass core, for example Type FT600 URT, Spectrum (SLT), No. BF05900 available from 3M, USA. The buffer layer 18 is preferably partially stripped back a short distance (e.g., approx. 1 cm) from the fiber tip 34 so that the diameter of the optical fiber 12 in the region around the fiber tip 34 is approximately 0.6 mm. For efficient operation of the device the surface quality of the fiber tip 34 is high. The fiber tip 34 is preferably substantially free from defects within a central aperture of 88% of the diameter of the fiber optic core 32 with all sharp edges having been previously removed from the fiber tip 34. Preferably, other defects (if present) do not scatter light outside a 0.37 numerical aperture (NA), and do not cause localized heating when illuminated with 60 W of laser light at 810 nm evenly distributed over a 0.37 NA. The optical fiber 12 is preferably capable of withstanding a force of 2 kg, applied between the connector/terminator (SMA) 22, and the distal end 13, without damage.

The relationship between the position of the markings or indicators 45, 46 and an introducer sheath 40 or the like will now be described in more detail with reference to FIGS. 3(a) and (b).

Figure 3A:
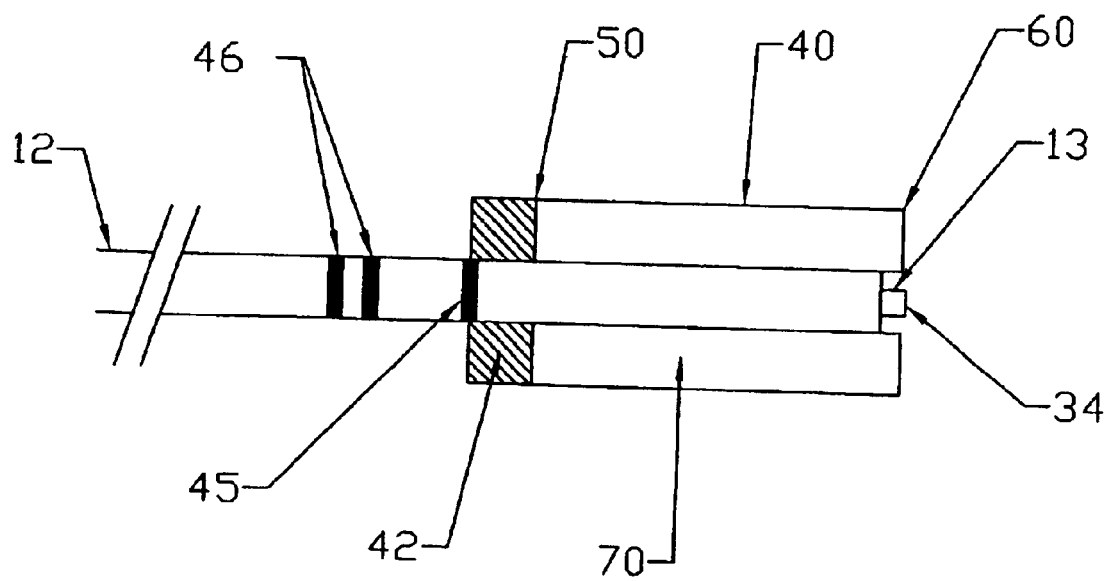
FIG. 3(a) shows an optical fiber having been initially inserted into an introducer sheath and FIG. 3(b) shows the introducer sheath having been subsequently withdrawn relative to the optical fiber.
Figure 3B:
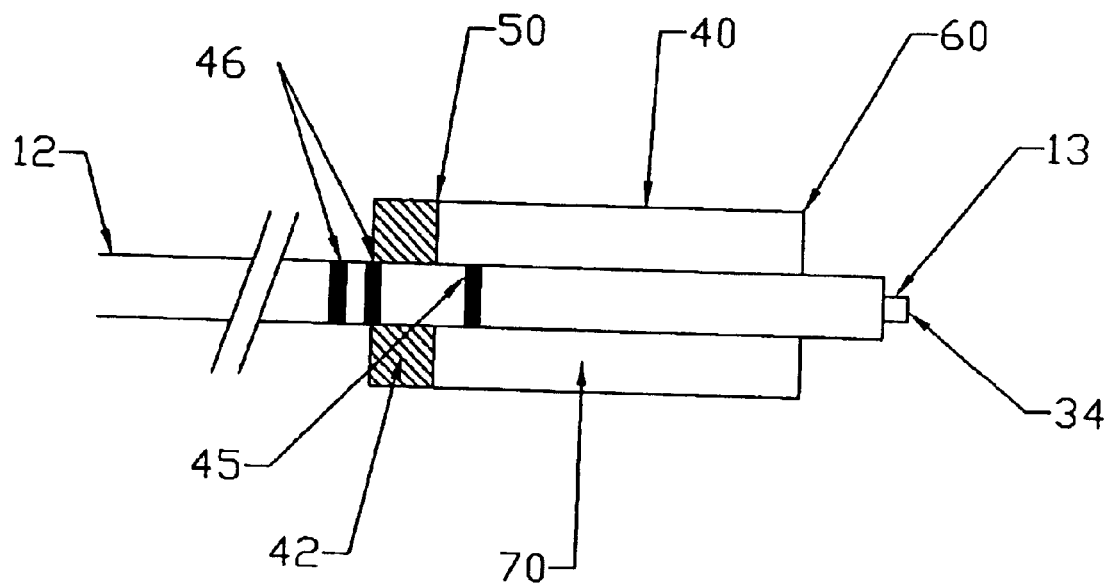

FIG. 3a shows the optical fiber 12 having been initially inserted within an introducer sheath 40 so that the distal end 13 of the optical fiber 12 is substantially flush or otherwise aligned with the distal end 60 of the introducer sheath 40. Marking 45 is shown substantially aligned with the proximal end 50 of the introducer sheath 40. The introducer sheath 40 is then withdrawn relative to the optical fiber 12 until marking 46 is substantially aligned with the proximal end 50 of the introducer sheath 40. As shown in FIG. 3(b), the distal end 13 of the optical fiber 12 then protrudes beyond the distal end 60 of the introducer sheath 40 by a predetermined amount, preferably approx. 3 cm.

The introducer sheath 40 comprises a hollow tube 70 with a friction seal 42 at the proximal end 50 to prevent blood loss during insertion into blood vessels. The placement of the introducer sheath 40 through skin and tissue provides access into an area to be treated, and acts as a guide for introducing instrumentation and other apparatus. The introducer sheath 40 is preferably a five French introducer sheath, such as RCF-50-35-45-J-RB available from Cook, Inc., Bloomington, Ind.

Markings or indicators 45, 46 are preferably optically visual markings which are preferably provided around the whole circumference of the protective buffer layer 18 of the optical fiber 12, and are provided at predetermined distance from the distal end 13 of the optical fiber 12. The predetermined distances are arranged to correspond to predetermined positions of the distal end 13 of the optical fiber 12 relative to the distal end 60 of the introducer 40. The predetermined position represent both alignment of the respective distal ends 13, 60 as shown in FIG. 3(a) and also protrusion of the distal end 13 of the optical fiber 12 beyond the distal end 60 of the introducer 40 as shown in FIG. 3(b).

In one embodiment the markings or indicators 45, 46 may be engraved or embossed onto the protective buffer layer 18 of the optical fiber 12 surface. Advantageously, this enables an operator to have tactile feedback as to the position of the marking. 45, 46 and thus have an indication as to the position of the optical fiber 12 within the introducer sheath 40, without necessarily having to look at the optical fiber 12.

The markings 45, 46 preferably comprise one or more bands provided at a number of predetermined locations and may preferably be provided by heat shrinking material onto the optical fiber 12. The bands are preferably 1 mm wide with±0.5 mm tolerance. The bands are preferably colored in order to contrast with the color of the buffer layer 18. The number of bands can give information about the location. For example, one band may be provided as a first marker 45, and two bands for a second marker 46 etc.

The location of the first marker 45 preferably corresponds to a depth of insertion of the optical fiber 12 into the introducer sheath 40 such that the distal end 13 of the optical fiber 12 (i.e. fiber tip 34) is very closely aligned or is substantially flush with the distal end 60 of the introducer sheath 40. The introducer sheath 40 is preferably 35 cm or 45 cm long and may be provided with a 2.1 cm friction seal 42 making a total length 37.1 cm or 47.1 cm. Accordingly, the first marking 45 may be provided at 371 mm±1 mm or 471 mm±1 mm from the distal end 13 of the optical fiber 12.

The location of the second marking 46 preferably corresponds to a position where the distal end 13 of the optical fiber 12 extends or projects 30 mm±1 mm beyond the distal end 60 of the introducer sheath 40. Accordingly, the second marking is preferably provided at 401 mm±1 mm or 501 mm±1 mm from the distal end 13 of the optical fiber 12.

The markings 45, 46 may comprise any number of bands, color, forms for ease of recognition during a medical procedure, or be provided at other locations along the optical fiber 12 depending upon the length of the introducer sheath 40 and any friction seal that the optical fiber 12 is required to cooperate with.

Figure 4:
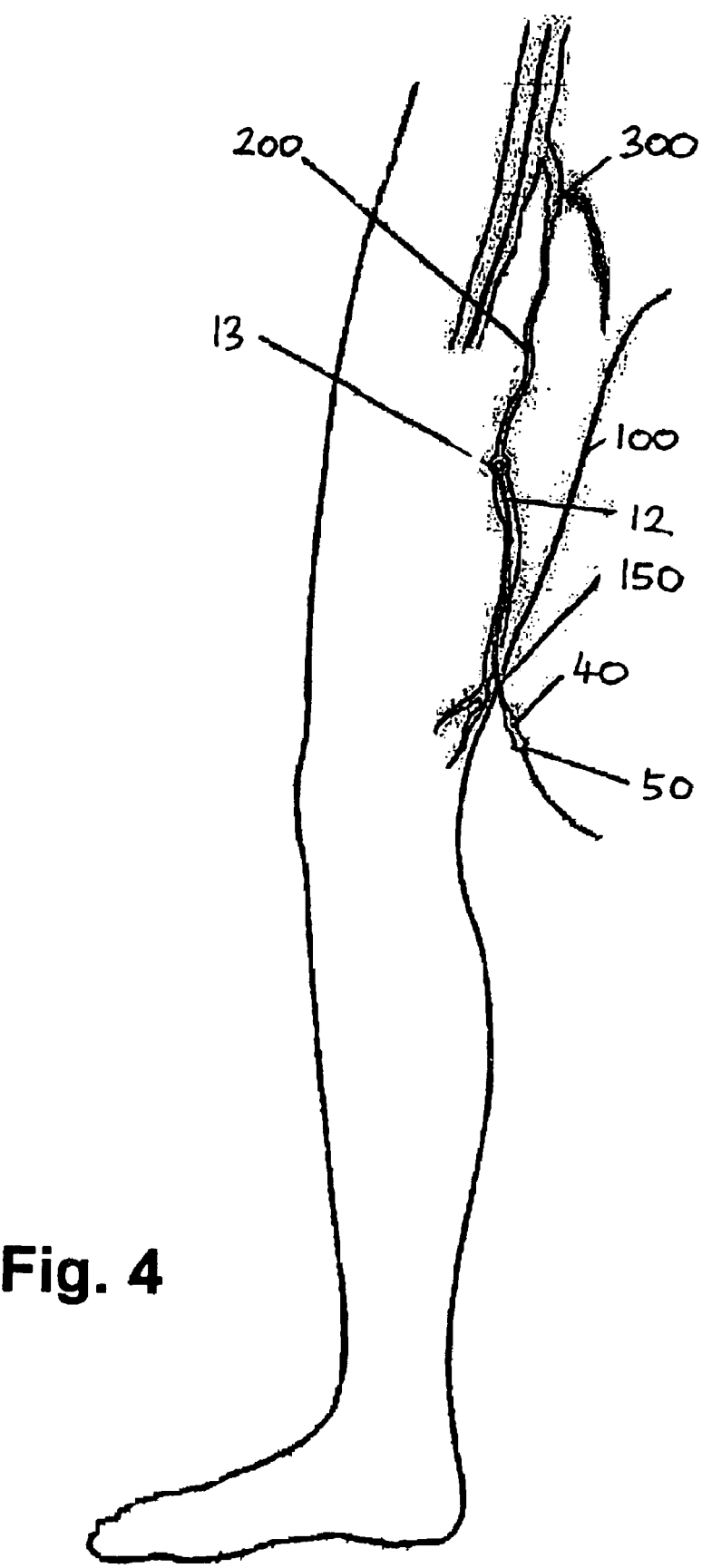
FIG. 4 shows the optical fiber and introducer sheath used for endovenous laser treatment.

An example of a use of the medical laser device is for use in endovenous laser treatment (EVLT) in a human leg 100. This will now be described in more detail with reference to FIG. 4. Local anaesthesia such as 0.3% or otherwise dilute lidocaine administered perivenously along the Greater Saphenous Vein (GSV) 200 and ultrasound guidance, are preferably used. Percutaneous entry into the Greater Saphenous Vein 200 is made with a needle at point 150, 25–45 cm below the Saphenofemoral Junction (SFJ) 300. A 0.035" (0.089 cm) J-tip guide wire is passed into the Greater Saphenous Vein 200 and a five French introducer sheath 40 is passed over the guide wire and up to the Saphenofemoral Junction 300. The guide wire is removed and a sterile 600 pm diameter core, bare-tipped optical fiber 12 is introduced into the vein 200 through the introducer sheath 40 until the first marking 45 is aligned with the proximal end 50 of the introducer sheath 40 (which corresponds with the portion of the friction seal furthermost from distal end 60). The optical fiber 12 and the proximal end 50 of the introducer sheath 40 are then fixed or held together. They are then moved together and positioned using ultrasound guidance at a location about 1–2 cm below the Saphenofemoral Junction 300 within the Greater Saphenous Vein 200. Once positioned, the introducer sheath 40 is then released from the optical fiber 12 and the introducer sheath 40 is withdrawn relative to the optical fiber 12 until the proximal end 50 of the introducer sheath 40 is aligned with the second mark 46 on the optical fiber 12. When the introducer sheath 40 and the optical fiber 12 are in this position then the distal end 13 of the optical fiber will extend approximately 30 mm beyond the distal end 60 of the introducer sheath 40. This position has been found to be an effective position for administering laser energy in EVLT treatment. An extension of 20 mm of the optical fiber 12 beyond the end of the introducer sheath 40 has been found to be the minimum suitable distance for administering laser energy in EVLT treatment without causing thermal damage to the introducer sheath 40. The optical fiber 12 and the proximal end 50 of the introducer sheath 40 are then secured together with non-permanent means. Alternatively, if marking 45 is embossed then there may be sufficient co-operation between the marking 45 and the friction seal 42 of the introducer sheath 40 to secure them temporarily together. Pulsed 810 nm wavelength laser radiation from a laser energy source (not shown) is administered with a power of 10–12 Watts, in pulses of 0.8–1.0 second duration at 1 second pulse intervals to treat the Greater Saphenous Vein 200. The introducer sheath 40 together with the optical fiber 12 are then slowly withdrawn in preferably 2–5 mm increments whilst administering the laser radiation, and manual compression is applied over a red aiming beam in order to achieve vein wall apposition around the laser fiber tip 34.

In an embodiment, the cycle is activated and deactivated by a foot switch or hand switch. The clinician is instructed to withdraw the introducer sheath 40 2–3 mm between 1 second laser pulses. This process continues until the desired length of the vein has been treated.

In other embodiments the optical fiber 12 may be made of materials or comprise material combinations other than glass so long as the guiding properties of the core 32 of the optical fiber 12 are maintained i.e. providing the core 32 has a higher refractive index than the cladding 30, and so long as the materials can operate in the temperature range −10° C. to 120° C. For example any glass, plastic or hollow waveguide material could be used.

It will also be appreciated that the indicators or markings 45, 46 may be ink markings and the color of the markings 45, 46 may give information about their location. For example the first marker 45 may be colored differently to the second marker 46. Alternatively, according to less preferred embodiments, the markings 45, 46 may be radio opaque and hence be capable of observation by non-optical means.

Furthermore, it will be appreciated that other introducer sheaths commonly used in the art in interventional cardiology and electrophysiology procedures including angiography, angioplasty, stenting, atherectomy, temporary pacing, endomyocardial biopsies, transseptal catheterizations, electrophysiology studies, and RF ablations could be used.

Another embodiment of the present invention is contemplated, wherein the laser provides a continuous rather than pulsed output. The laser may be activated by a foot or hand switch. Graduated markings are provided on the external surface of the introducer sheath 40 to provide control for withdrawing the introducer sheath 40 at a prescribed rate and to indicate how far the introducer sheath 40 has been withdrawn from the patient's body. A visible and/or audible indicator may be provided so as to assist an operator to remove the introducer sheath 40 and optical fiber 12 at a controlled speed. In one embodiment the visible and/or audible indicator may form part of the laser system coupled to the optical fiber 12. As an example, if the markings on the external surface of the introducer sheath 40 were placed at 1 cm intervals, then the audible and/or visual indicator might be activated once per second thereby assisting a user to withdraw the introducer sheath 40 and optical fiber 12 at a controlled speed of 1 cm/sec. An additional graduation on the introducer sheath 40 would therefore be revealed every time the indicator bleeped and/or flashed.

This embodiment has the benefit of potentially providing bio-feedback to control the rate at which the introducer sheath 40 is withdrawn. Furthermore, the continuous withdrawal results in a more uniform illumination of the internal surface of the blood vessel. According to the previously described embodiment using a pulsed laser source, the introducer sheath 40 and optical fiber 12 are withdrawn in a stepped manner which may in some circumstances cause relatively high intensity regions of illumination at, for example, 2–3 mm intervals along the blood vessel. Any such potential problem is therefore avoided by using a continuous laser source, providing graduations on the introducer sheath 40 and withdrawing the introducer sheath 40 in a controlled manner.

According to a further embodiment a visual and/or audible indicator may also be used in conjunction with the previously described embodiment which uses a pulsed laser source as an aid to withdrawing the introducer sheath 40. This allows a hybrid approach wherein the optical fiber 12 is withdrawn a longer distance e.g. 1–3 cm during a longer pulse-length. According to this embodiment, the laser source is operated in a quasi-continuous mode.

It will be appreciated that the above described embodiments are given by way of example only and that various modifications thereto may be made without departing from the scope of the invention.

What is claimed is:

1. A method of endovenous laser treatment comprising:
   (a) introducing an introducer sheath into a blood vessel, the introducer sheath having a distal end, a proximal end and graduated markings along a portion thereof;
   (b) extending a distal tip of an optical fiber through the introducer sheath; and
   (c) withdrawing the introducer sheath and the optical fiber from the blood vessel at a desired rate by controlling exposure of the graduated markings.

2. The method of endovenous laser treatment of claim 1, wherein during said withdrawing step, the introducer sheath and the optical fiber are withdrawn along the blood vessel a certain distance.

3. The method of endovenous laser treatment of claim 1, further comprising synchronizing exposure of the graduated markings as the introducer sheath is withdrawn from the blood vessel to a timing indicator.

4. The method of endovenous laser treatment of claim 3, wherein the timing indicator is a visual indicator.

5. The method of endovenous laser treatment of claim 3, wherein the timing indicator is an audible indicator.

6. The method of endovenous laser treatment of claim 1, further comprising passing laser radiation down the optical fiber.

7. The method of endovenous laser treatment of claim 6, further comprising repeating said passing laser radiation and withdrawing steps a plurality of times.

8. The method of endovenous laser treatment of claim 6, wherein the laser radiation is delivered in a substantially continuous manner.

9. The method of endovenous laser treatment of claim 6, wherein the laser radiation is delivered in a pulsed manner.

10. The method of endovenous laser treatment of claim 6, wherein the laser radiation is delivered in a quasi-continuous manner.

11. The medical laser device of claim 6, wherein during said withdrawing step laser radiation is emitted from the optical fiber into the blood vessel.

12. The method of endovenous laser treatment of claim 1, wherein the optical fiber has a first indicator and further comprising positioning the first indicator on the optical fiber adjacent the proximal end of the introducer sheath so that the distal tip of the optical fiber does not project beyond the distal end of the introducer sheath.

13. The method of endovenous laser treatment of claim 12, wherein the optical fiber has a second indicator and further comprising positioning the second indicator on the optical fiber adjacent the proximal end of the introducer sheath so that the distal tip of the optical fiber extends beyond the distal end of the introducer sheath.

14. The method of endovenous laser treatment of claim 1, wherein the distal tip of the optical fiber projects beyond the distal end of the introducer sheath prior to step (c).

15. The method of endovenous laser treatment of claim 1, wherein the distal tip of the optical fiber is introduced into the introducer sheath after the introducer sheath has been introduced into the blood vessel.

16. The method of endovenous laser treatment of claim 1, wherein the proximal end of the introducer sheath is external to the blood vessel.

17. The method of endovenous laser treatment of claim 1, wherein the graduated markings are uniformly spaced.

18. The method of endovenous laser treatment of claim 17, wherein the graduated markings have a 1 cm spacing.

19. The method of endovenous laser treatment of claim 1, wherein during said withdrawing step, the introducer sheath is withdrawn so that the graduated markings are exposed to a user at a predetermined rate.

20. A method of endovenous laser treatment comprising:
 (a) introducing an introducer sheath into a blood vessel having an inner wall, the introducer sheath having a distal end, a proximal end and graduated markings along a portion thereof;
 (b) introducing a distal tip of an optical fiber into the introducer sheath, the optical fiber also having a proximal end, a first indicator that indicates a first position of the distal tip of the optical fiber relative to the introducer sheath, and a second indicator that indicates a second position of the distal tip relative to the introducer sheath;
 (c) positioning the first indicator on the optical fiber adjacent the proximal end of the introducer sheath so that the distal tip of the optical fiber does not project beyond the distal end of the introducer sheath;
 (d) positioning the second indicator on the optical fiber adjacent the proximal end of the introducer sheath so that the distal tip of the optical fiber projects beyond the distal end of the introducer sheath a predetermined distance; and
 (e) withdrawing, after said step (d), the introducer sheath from the blood vessel at a desired rate by controlling exposure of the graduated markings.

* * * * *